United States Patent
Morohashi et al.

(10) Patent No.: US 6,458,960 B1
(45) Date of Patent: Oct. 1, 2002

(54) SULFONAMIDE DERIVATIVES

(75) Inventors: Hirohisa Morohashi; Hiroshi Sato, both of Saitama (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/717,686

(22) Filed: Nov. 21, 2000

Related U.S. Application Data

(62) Division of application No. 09/423,950, filed as application No. PCT/JP98/02372 on May 29, 1998, now Pat. No. 6,180,796.

(30) Foreign Application Priority Data

May 30, 1997 (JP) .............................. 9-156156

(51) Int. Cl.⁷ ................... C07D 277/00; C07D 261/00; C07D 231/10; A61K 31/415; A61K 31/42
(52) U.S. Cl. .................. 548/200; 548/214; 548/236; 548/248; 548/333.5; 548/374.1; 548/335.5; 514/406; 514/365; 514/372; 514/374; 514/399; 514/378
(58) Field of Search ............... 548/200, 214, 548/236, 333.5, 248, 374.1; 514/406, 365, 372, 374, 399, 378

(56) References Cited

U.S. PATENT DOCUMENTS 5,250,549 A * 10/1993 Yoshino et al. ............. 514/345
5,840,895 A    11/1998 Ohtsuka et al. ............ 544/366

FOREIGN PATENT DOCUMENTS

EP    0 472 053    2/1992
JP    5-39256      2/1993

OTHER PUBLICATIONS

Simov, D. et al.;Izv Khim., 14/1, 131–4(1981), also cited as CAPLUS 1982:85186, Teaction of 1phenylsulfonyl–2(H) . . .*

Koyanagi et al" In Vivo Tumor Growth Inhibi. produced by Novel Sulfonamide . . . "; Cancer Res.54, 1702(1994).*
Cancer Research 54, 1702–1706, Apr. 1, 1994; Nozomu Koyanagi, et al.; "In Vivo Tumor Growth Inhibition Produced by a Novel Sulfonamide, E7010, against Roden and Human Tumors".

* cited by examiner

Primary Examiner—Mukund J. Shah
Assistant Examiner—Sudhaker B. Patel
(74) Attorney, Agent, or Firm—Nields & Lemack

(57) ABSTRACT

The present invention relates to a compound of the following Formula (1) or the pharmaceutically acceptable salts thereof, having low toxicity and a potent effect of inhibiting tubulin polymerization, and the use thereof as a pharmaceutical composition:

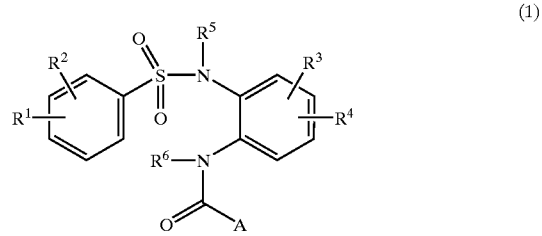

(1)

(wherein $R^1$ and $R^2$ may be the same or different and each independently represents a hydrogen atom, a halogen atom, a lower alkyl group, a lower alkoxy group, a nitro group, a hydroxy group; each $R^3$, $R^4$, $R^5$ and $R^6$ represents a hydrogen atom; A represents any group of (1) 5-membered heterocyclic group (except triazoyl group) optionally substituted by a lower alkyl group or phenyl group whose ring members include at least 1 nitrogen atom and may include any atom(s) selected from the group consisting of nitrogen atom, oxygen atom, and sulfur atom, and (2) a 3 to 10-membered alicyclic group whose ring members include at least 1 nitrogen atom and may include any atom(s) selected from the group consisting of nitrogen atom, oxygen atom, and sulfur atom).

6 Claims, No Drawings

SULFONAMIDE DERIVATIVES

This application is a Divisional of U.S. patent application Ser. No. 09/423,950 filed Nov. 15, 1999, now U.S. Patent No. 6,180,796, which is a §371 of PCT/JP98/02372 filed May 29, 1998 claiming priority of Japanese Patent Application No. 9-156156 filed May 30, 1997.

TECHNICAL FIELD

The present invention relates to sulfonamide derivatives having tubulin polymerization inhibitory activity, and tubulin polymerization inhibitory agents, anticancer agents, and agents useful as preventives or remedies for rheumatism such as inflammatory rheumatism containing these derivatives as the active ingredients.

BACKGROUND ART

Rheumatism is a refractory disease. Rheumatoid arthritis (RA), for example, has the basal lesion in proliferation of synovial cells accompanied with abnormalities in immune system caused by various factors. RA often causes progressive dysfunctions in articulation. To prevent from dysfunctions by RA, which is considered to be an auto immune disease, agents correcting immune abnormalities are used in combination to general antiphlogistics under the expectation of altering natural couse of RA.

For remedy of arthritis, steroidal agents such as adrenocortical hormones including cortisone, non-steroidal anti-inflammatory agents such as aspirin, piroxicam and indometacin, antirheumatic agents such as gold preparations including aurothiomalate, D-penicillamines, and immunosuppressive agents such as cyclophosphamide and azathioprine have been used.

Recent Japanese reports suggest that an intermittent administration in low dose of methotrexate(MTX) result in high efficiency and rapid response. However, it has many side effects including interstitial pneumonia, stomatitis, gastrointestinal symptons such as nausea and vomition, fibrous liver, and marrow suppression. Furthermore, a long term of the therapeutic administrations may cause high infectiousness and complicated malignancy. There has been found no desirable drug which is really effective and has little side effects with respect to this disease.

Although many compounds having tubulin polymerization inhibitory activity have been reported, nothing but colchicine(an arthrifuge) and vincristine(an antineoplastic) (Cancer Reseach, vol.20, p1023, 1960) among them are applicable for therapeutic agents. Rheumacon, the glycoside extracted from the natural material having antirheumatic effect is reported to show tubulin polymerization inhibitory effect(British Journal of rheumatology, Vol.32, p804, 1993), but it has the unknown chemical structural formula and many side effects such as moon face, suffusion, and gastrointestinal disorder are reported.

The JP Laid-Open No.39256/1993 discloses that the other sulfonamides than those of the present invention are useful antineoplastics. N-[2-((4-hydroxyphenyil) amino)-3-pyridinyl]-4-methoxybenzenesulfonamide described in the publication is reported to show tubulin polymerization inhibitory effect (Cancer Research, Vol.54, p1702, 1994).

However, the above agent has the severe side effects which make impossible its continuous administrations, the poor sustained therapeutic effects, or no effects for some patients. The clinical therapy demands low toxic agents which can protect and remedy patients from RA through new mechanism.

DISCLOSURE OF THE INVENTION

For solving the above problem, the present inventors made diligent studies to achieve low toxic anticancer agents and agents useful as preventives or remedies for rheumatism such as inflammatory rheumatism. As the result, it has been found that the novel sulfonamides derivatives having tubulin polymerization inhibitory activity as described below are lowly toxic, effective as anticancer agents, and useful as preventives or remedies for rheumatism such as inflammatory rheumatism. This finding has led to the completion of the present invention.

The compounds of the present invention as shown by the general formula(1) are novel(except the case that A is triazol in the formula(1) ) and their medical uses are unknown together with the case that A is triazol.

The present invention relates to the foliowing(i) to (x i).

(i) Sulfonamide derivatives represented by the general formula(1)

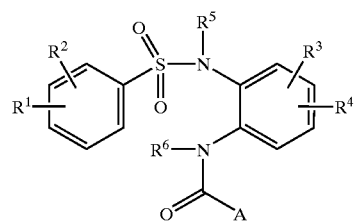

(1)

[wherein $R^1$, $R^2$ may be the same or different and each independently represents a hydrogen atom, a halogen atom, a lower alkyl group, a lower alkoxy group, a nitro group, a hydroxy group, a cyano group, a $C_1$ to $C_8$ acyl group, an optionally substituted phenoxy group, or an optionally substituted amino group;

$R^3$, $R^4$ may be the same or different and each independently represents a hydrogen atom, a halogen atom, a lower alkyl group, a lower alkoxy group, a nitro group, a hydroxy group, a group as shown by the general formula(2) described below:

(wherein $R^7$ represents a hydrogen atom, a hydroxy group, a lower alkyl group, a lower alkoxy group, or an optionally substituted amino group, and n means an integer of 1–5), a group as shown by the general formula(3) described below:

(wherein B represents an imidazolyl group, a triazolyl group, a tetrazolyl group, or an optionally substituted amino group, and n means any integer of 1–5), a group as shown by the general formula(4) described below:

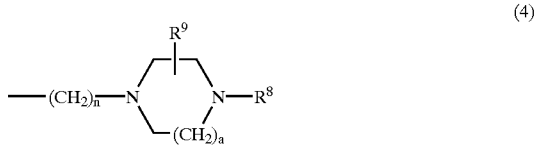

(wherein $R^8$ represents a lower alkyl group, a $C_1$ to $C_5$ alkyl group substituted by 1 or 2 hydroxy group(s), a $C_1$ to $C_5$ alkyl group substituted by a $C_1$ to $C_5$ alkoxycarbonyl group, a $C_1$ to $C_5$ acyl group, or a pyridyl group; $R^9$ represents a lower alkyl group or a hydroxy group; a and n means any integer of 0–3 and 0–6 respectively), a group as shown by the general formula(5) described below:

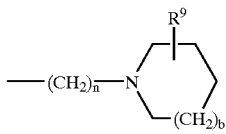
(5)

(wherein $R^9$ represents a lower alkyl group or a hydroxy group; b and n means any integer of 0–3 and 0–6 respectively), a group as shown by the general formula(6) described below:

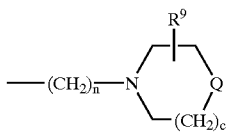
(6)

(wherein $R^9$ represents a lower alkyl group or a hydroxy group; c and n means any integer of 0–3 and 0–6 respectively; Q represents an oxygen atom, a sulfur atom, or a group as shown by the general formula(7) described below:

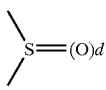
(7)

(wherein d means 1 or 2) ), a group as shown by the general formula(8) described below:

—(CH$_2$)$_n$—N R$^{10}$ R$^{11}$ (8)

(wherein $R^{10}$, $R^{11}$ may be the same or different and each independently represents a hydrogen atom, a lower alkyl group or an optionally substituted amino lower alkyl group; n means any integer of 0–6), a group as shown by the general formula(9) described below:

—(CH$_2$)$_n$—S(O)$_e$—R$^{12}$ (9)

(wherein $R^{12}$ represents a hydrogen atom, a lower alkyl group or an aryl group, an aralkyl group or an optionally substituted amino group; e and n means any integer of 0–3 and 0–6 respectively) or a group as shown by the general formula(10) described below:

—(CH$_2$)$_n$—OR$^{13}$ (10)

(wherein $R^{13}$ represents a hydrogen atom, a lower alkyl group or an acyl group, a phosphate group or an optionally substituted aminoalkyl group; and n means any integer of 1–6), $R^5$, $R^6$ may be the same or different and each independently represents a hydrogen atom, a halogen atom, a lower alkyl group, an acyl group, or an optionally substituted amino group; A represents any group of (1) an optionally substituted 5-membered heterocyclic group (except triazol) whose ring members include at least 1 nitrogen atom and may include any atom(s) selected from the group consisting of nitrogen atom, oxygen atom, and sulfur atom, (2) an optionally substituted alicyclic group, and (3) an alicyclic group whose ring members include at least 1 nitrogen atom and may include any atom(s) selected from the group consisting of nitrogen atom, oxygen atom, and sulfur atom], and the pharmaceutically acceptable salts thereof.

(ii) Sulfonamide derivatives as defined in (i), wherein $R^1$ is a lower alkoxy group, and $R^2$, $R^3$, $R^4$, $R^5$, and $R^6$ may be the same or different and each independently represents a hydrogen atom, a halogen atom, a lower alkyl group, or an optionally substituted amino group, and the pharmaceutically acceptable salts thereof.

(iii) Sulfonamide derivatives as defined in (i), wherein $R^1$ is a lower alkoxy group, and $R^2$ $R^3$, $R^4$ $R^5$ and $R^6$ may be the same or different and each independently represents a hydrogen atom, a halogen atom, a lower alkyl group, or an optionally substituted amino group, and A represents an optionally substituted 5-membered heterocyclic group (except triazol) whose ring members include at least 1 nitrogen atom and may include any atom(s) selected from the group consisting of nitrogen atom, oxygen atom, and sulfur atom, and the pharmaceutically acceptable salts thereof.

(iv) Sulfonamide derivatives as defined in any one of (i)–(iii), wherein A represents an optionally substituted isoxazol group, and the pharmaceutically acceptable salts thereof.

(v) Sulfonamide derivatives as defined in (iv), wherein A represents a 4-isoxazol group which has at least one lower alkyl group at the 3- and 5- position, and the pharmaceutically acceptable salts thereof.

(vi) Sulfonamide derivatives as defined in (i), wherein $R^1$ is a lower alkoxy group which is located at the para-position, and $R^2$ to $R^6$ are hydrogen atoms, and the pharmaceutically acceptable salts thereof.

(vii) A pharmaceutical composition containing as an active ingredient the sulfonamide derivatives (including the case that A is triazolyl group in the general formula(1)) as defined in any one of (i)–(vi), or the pharmaceutically acceptable salts thereof.

(viii) A tubulin polymerization inhibitory agent containing as an active ingredient the sulfonamide derivatives (including case that A is triazolyl group in the general formula(1)) as defined in any one of (i)–(vi), or the pharmaceutically acceptable salts thereof.

(ix) An anticancer agent containing as an active ingredient the sulfonamide derivatives (including the case that A is triazolyl group in the general formula(1)) as defined in any one of (i)–(vi), or the pharmaceutically acceptable salts thereof.

(x) A drug as a preventive or a remedy for rheumatism containing as an active ingredient the sulfonamide derivatives (including the case that A is triazolyl group in the general formula(1)) as defined in any one of (i)–(vi), or the pharmaceutically acceptable salts thereof.

(xi) A drug as a preventive or a remedy for rheumatism as defined in (x), wherein rheumatism is inflammatory rheumatism.

BEST MODE FOR CARRYING OUT THE INVENTION

The present invention will be more particularly described below.

Lower alkyl groups of the present invention are $C_1$–$C_6$ straight chain or branched alkyl groups including methyl group, ethyl group, n-propyl group, isopropyl group, nbutyl group, sec-butyl group, tert-butyl group, n-pentyl group, amyl group, isopentyl group, neopentyl group, tert-pentyl group, 1-methylbutyl group, 2-methylbutyl group, 1,2-dimethylpropyl group, n-hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-metylpropyl group. These groups may have Additional substituents as long as they provide no special interference. $C_1$–$C_4$ alkyl groups are preferable, C–$C_3$ alkyl groups are more preferable, and methyl group and ethyl group are the most preferable.

Lower alkoxy groups of the present invention are $C_1$–$C_6$ straight chain or branched alkoxy groups including methoxy group, ethoxy group, isopropoxy group, n-butoxy group, isobutoxy group, tert-butoxy group. These groups may have additional substituents as long as they provide no special interference. $C_1$–$C_4$ alkoxy groups are preferable, $C_1$–$C_3$ alkoxy groups are more preferable, and methoxy group and ethoxy group are the most preferable.

Halogen atoms of the present invention includes fluorine atom, chlorine atom, and bromine atom.

Substituents connected to nitrogen atoms, for example,to those found in amino groups include lower alkyl groups, and $C_1$–$C_8$ acyl groups (including $C_1$–$C_8$ alkoxycarbonyl group). These groups may have additional substituents as long as they provide no special interference.

Optionally substituted amino groups include unsubstituted amino group, lower acylamino groups (for example, amino groups substituted with $C_1$–$C_4$ acyl groups such as formylamino group, propionylamino group), optionally substituted alkoxycarbonylamino groups (for example, benzyloxycarbonylamino group), and mono- or di-lower alkylamino groups (for example, N,N-dimethyl-amino group, N,N-diethylamino group, N,N-dipropylamino group, N,N-diisopropylamino group, N,N-di-n-butylamino group). optionally substituted aminoalkyl groups include unsubstituted aminoalkyl groups and mono- or di-lower alkyl substituted aminoalkyl groups ($C_1$–$C_{10}$)such as N,N-diethylaminoethyl group, N,N-dimethylaminomethyl group, N,N-dimethylaminoethyl group, and N,N-dimethylaminoethyl group.

Alicyclic hydrocarbon groups (groups represented by removing onehydrogenatomfromthecorrespondingalicyclic hydrocarbon), which are included in A of the present invention, include 3 to 10-membered alicyclic hydrocarbon groups such as cyclopropyl group, cyclobutyl group, cyclopentyl group, cyclohexyl group, and cycloheptyl group. 5 to 7-membered alicyclic hydrocarbon groups such as cyclohexyl group, cycloheptyl, and cycloheptyl group are preferable.

5-membered Heterocyclic hydrocarbon groups having at least one nitrogen atom, which are included in A of the present invention, mean groups represented by removing one hydrogen atom from any carbon atom of the corresponding 5-membered heterocyclic hydrocarbon rings, which have at least-two unsaturated bond and contain preferably at least two heteroatoms. They include pyrrolyl group, oxazolyl group, isoxazolyl group, thiazolyl group, isothiazolyl group, imidazolyl group, pyrazolyl group, oxadiazolyl group, thiadiazolyl group, triazolyl group, and tetrazolyl group. Oxazolyl group, isoxazolyl group, and isothiazolyl group are preferable, and isoxazolyl group is more preferable.

Alicyclic hydrocarbon groups having at least one nitrogen atom in the rings, which are included in A of the present invention, mean groups represented by removing one hydrogen atom from any carbon atom of the corresponding alicyclic hydrocarbon rings, which may have one unsaturated bond and contain preferably at least two heteroatoms. The heteroatom may be selected from the group containing of nitrogen atom, oxygen atom, and sulfur atom. They include 3 to 10-membered alicyclic hydrocarbon groups having at least one nitrogen atom in the rings such as aziridinyl group, azethidinyl group, pyrrolidinyl group, piperidinyl group, oxazolinyl group, isoxazolidinyl group, thiazolidinyl group, imidazolidinyl group, and pyrrazolidinyl group. Thiazolidinyl group is preferable.

Substituents of the present invention bonding to any carbon atom of alkyl groups or cyclic (optionally containing hetero atom(s)) hydrocarbon groups include lower alkyl groups, lower alkoxy groups, optionally substituted amino groups, halogen atoms, nitro groups, hydroxy group, carboxyl groups, acyl groups (including optionally phenyl-substituted alkoxycarbonyl), cyano group, and phenyl group. These groups may have additional substituents as long as they provide no special interference. Lower alkyl groups are preferable for substituents of the groups A.

Acyl groups of the present invention include $C_1$–$C_8$ acyl groups such as formyl group, acetyl group, propionyl group, butyryl group, valeryl group, optionally substituted benzoyl group, and optionally substituted benzyloxycarbonyl group. Substituents bonding to the benzoyl group or the benzyloxycarbonyl group include the substituents bonding to the carbon atom as described above.

Substituents bonding to optionally substituted phenoxy group of the present invention include the substituents bonding to the carbon atom as described above.

Optionally substituted amino lower alkyl groups of the present invention include $C_1$–$C_3$ alkylamino-substituted $C_1$–$C_3$ alkyl groups, alicyclic alkylamino-substituted $C_1$–$C_3$ alkyl groups, and aromatic amino-substituted $C_1$–$C_3$ alkyl groups where alicyclic alkyl groups include $C_3$–$C_6$ groups such as cyclopropyl group, cyclobutyl group, cyclopentyl group and cyclohexyl group, and aromatic groups include $C_1$–$C_{10}$ groups such as phenyl group and naphthyl group.

Aralkyl groups of the present invention include $C_7$–$C_{11}$ groups such as benzyl group.

—(CH$_2$)$_n$-groups of the present invention include methylene group, dimethylene group, trimethylene group, and tetramethylene group.

The groups as shown by the general formula (2) include carboxymetyl group, methoxycarbonylmethyl group.

The groups as shown by the general formula (3) include imidazolylmethyl group, triazolylmethyl group, tetrazolylmethyl group, aminoethyl group.

The groups as shown by the general formula(4) include 4-methyl-3-methylpiperadinylmethyl group.

The groups as shown by the general formula(5) include 4-methyl piperidinyl methyl group.

The groups as shown by the general formula(6) include 1-morphorino methyl group.

The groups as shown by the general foraula(8) include dimethylaminoethyl group.

The groups as shown by the general formula(9) include sulfonylmethyl group.

The groups as shown by the general formula (10) include hydroxy methyl group and methoxyethyl group.

In the present invention, preferable groups in $R^1$ are lower alkoxy groups located at the para position, and each preferable group in $R^2$, $R^3$, $R^4$, $R^5$, and $R^6$ is hydrogen atom. Preferable groups in A include thiazolidinyl group, $C_3$–$C_6$ alicyclic groups, pyrrolyl group, oxazolyl group, isoxazolyl group. Particularly preferable in A is 4-isoxazolyl group, which is more preferable if it has at least one substituent at the 3- and 5-position, and is the most preferable if it has methyl group or ethyl group both at the 3- and 5- positions. Preferable 4-isoxazolyl groups are, For example, 3-methyl-4-isoxazolyl group, 3,5-dimethyl-4-isoxazolyl group, 5-ethyl-3-methyl-4-isoxazolyl group, 3-ethyl-5-methyl-4-isoxazolyl group, 3,5-diethyl-4-isoxazolyl group. Combination of these preferable groups leads to the most preferable compound among all the sulfonamide derivatives as represented by the general formula(1).

Sulfonamide derivatives of the present invention may react with acids to form their salts, which are also covered by the present invention. Their salts include the salts of inorganic acids such as hydrogen chloride, hydrogen bromide, sulfuric acid and the salts of organic acids such as acetic acid, lactic acid, succinic acid, fumaric acid, maleic acid, citric acid, benzoic acid, methanesulfonic acid, p-toluenesulfonic acid.

The present invention covers all the hydrates and all the optical isomers, if any.

The compounds represented by the general formula(1) include:

(1) N-[2-(4-methoxybenzenesulfonamide)phenyl]-5-methyl-4-isoxazole carboxamide
(2) N-[2-(4-methoxybenzenesulfonamide)phenyl]-1,3-dimethyl-4-(1H-pyrazole)carboxamide
(3) N-[2-(4-methoxybenzenesulfonamide)phenyl]-2-methyl-4-thiazole carboxamide
(4) N-[2-(4-methoxybenzenesulfonamide)phenyl]-3-methyl-4-isothiazole carboxamide
(5) N-[2-(4-methoxybenzenesulfonamide)phenyl]-2,5-dimethyl-4-oxazole carboxamide
(6) N-[2-(4-methoxybenzenesulfonamide)phenyl]-1-methyl- 1H-imidazole-4-carboxamide
(7) N-[2-(toluenesulfonamide)phenyl]-5-methyl-4-isoxazole carboxamide
(8) N-[2-(benzenesulfonamide)phenyl]-5-methyl-4-isoxazole carboxamide
(9) N-[2-(4-fluorobenzenesulfonamide)phenyl]-5-methyl-4-isoxazole carboxamide
(10) N-[2-(4-nitrobenzenesulfonamide)phenyl]-5-methyl-4-isoxazole carboxamide
(11) N-[2-(3,4-dimethoxybenzenesulfonamide)phenyl]-5-methyl-4-isoxazole carboxamide
(12) N-[2-(4-methoxybenzenesulfonamide)phenyl]-(L)-prolinamide
(13) N-[2-(4-methoxybenzenesulfonamide)phenyl]-3,5-dimethyl-4-isoxazole carboxamide
(14) N-[2-(4-methoxybenzenesulfonamide)phenyl]-5-ethyl-4-isoxazole carboxamide
(15) (±)-N-[2-(4-methoxybenzenesulfonamide)phenyl]-4-thiazolidine carboxamide
(16) (±)-N-[2-(4-methoxybenzenesulfonamide)phenyl]-3-(N-methylpiperidine)carboxamide
(17) N-[2-(4-methoxybenzenesulfonamide)phenyl]-(D)-prolinamide (18) N-[2-(4-methoxybenzenesulfonamide)phenyl]-4-piperidine carboxamide
(19) (±)-N-[2-(4-methoxybenzenesulfonamide)phenyl]-3-piperidine carboxamide
(20) (±)-N-[2-(4-methoxybenzenesulfonamide)phenyl]-2-piperidine carboxamide
(21) N-[2-(4-methoxybenzenesulfonamide)phenyl]-5-methyl-4-oxazole carboxamide
(22) N-[2-(4-methoxybenzenesulfonamide)phenyl]-cyclohexyl carboxamide
(23) N-[2-(4-methoxybenzenesulfonamide)phenyl]-cyclopropyl carboxamide
(24) N-[2-(4-methoxybenzenesulfonamide)phenyl]-cyclobutyl carboxamide
(25) N-[2-(4-methoxybenzenesulfonamide)phenyl]-cyclopentyl carboxamide
(26) N-[2-(4-methoxybenzenesulfonamide)phenyl]-N-methyl-2-pyrrole carboxamide
(27) N-[2-(4-methoxybenzenesulfonamide)phenyl]-3-ethyl-5-methyl-4-isoxazole carboxamide
(28) N-[2-(4-methoxybenzenesulfonamide)phenyl]-5-ethyl-3-methyl-4-isoxazole carboxamide
(29) N-[2-(4-methoxybenzenesulfonamide)phenyl)-3,5-diethyl -4-isoxazole carboxamide
(30) N-$C_2$-(4-methoxybenzenesulfonamide)phenyl]-5-isopropyl-3-methyl-4-isoxazole carboxamide
(31) N-[2-(4-methoxybenzenesulfonamide)phenyl]-5-methyl- 3-phenyl-4-isoxazole carboxamide
(32) N-[2-(4-methoxybenzenesulfonamide)phenyl]-5-methyl-3-phenyl-4-isoxazole carboxamide The compounds of the present invention, which are novel and have not yet published in any documents, can be produced, for example, by the following reaction:

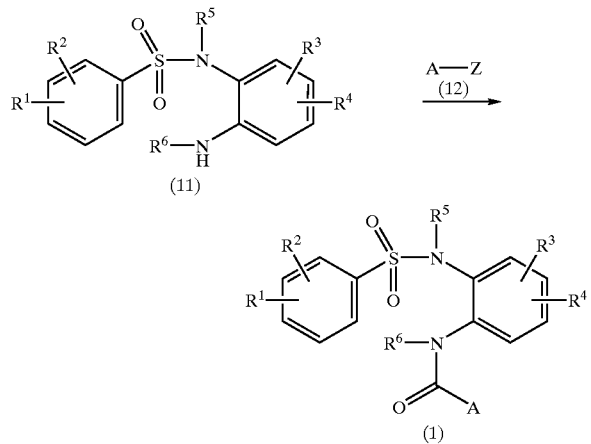

The novel sulfonamide derivatives represented by the general formula(1) can be produced by reacting compounds as shown by general formula(11) described below,

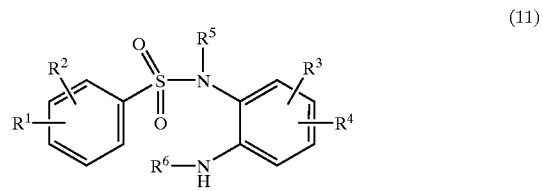

(wherein $R^1$, $R^2$, R3, $R^4$, $R^5$, and $R^6$ have the same meaning as mentioned before) with carboxylic acids or their reactive derivatives (whose functional groups may be protected if they are not associated with the reaction)as shown by general formula (12) described below, $$A—Z \quad (12)$$

(A has the same meaning as mentioned before, and Z represents carboxyl groups or the reactive groups derived therefrom).

The reaction is preferably carried out under the presence of a base.

Most of the compounds represented by the general formula(11) are known to the public, and the others can be prepared by the method JP Laid-Open No.39256/1993 has disclosed, or its modifications.

Any reactive derivatives that are generally used to form carboxamide bonds can be applied for reactive derivatives of carboxylic acids represented by the general formula(12). They include acid halides, active amides, and active esters. They may be prepared prior to the reaction or planned to form within the reaction system.

The acid halides, which include acid chloride and acid bromide, can be obtained generally by reacting carboxylic acids with thionyl halogenides.

For the active amides, there can be used acid amides of, for example, imidazole, pyrazole, 4-substituted imidazole, dimethylpyrazole, triazole, tetrazole, and benzothiazole.

For the active esters, there can be used acid esters which include methyl esters, methoxymethyl esters, cyanomethyl esters, propagyl esters, 4-nitrophenyl esters, 2,4-dinitrophenyl esters, and esters of, for example, 1-hydroxybenzotriazole.

The carboxylic acids represented by the general formusa (12) may be reacted with the amines represented by the general formula(11) under the presence of condensation agents such as N,N'-dicyclohexylcarbodiimide(DCC)and N-cyclohexyl-N-morpholino etylcarbodiimide. These reactions are preferably carried out under the presence of bases such as organic tertiary amines(for example, triethylamine, N,N-dimethylaniline, and pyridine).

The reaction solvents, which are desirable to use if they can dissolve the reaction-associated materials and have no reaction with them, include pyridine, tetrahydrofurane, dioxane, benzene, ether, methylene chloride, dimethylformamide, toluene, and the mixture solvents consisting of two or more solvents selected therefrom. But any reaction solvents can be used with no special limitation regardless of the above mentioned examples.

The reaction can be generally carried out at ambient temperature. Cooling or heating may be applied for the reaction if necessary. The reaction time is generally 5 min–20 hrs, and may be determined adequately depending upon materials and reaction temperature.

Deprotection such as acid treatment converts the reaction products, whose amino groups are protected, to the compounds represented by the general formula(1) which have the free amino groups.

The representative compounds as shown by the general formula(12) which are raw materials for syntheses include:

N-(2-aminophenyl)-4-methoxybenzenesulfonamide
N-(2-aminophenyl)-4-ethoxybenzenesulfonamide
N-(2-aminophenyl)-4-propoxybenzenesulfonamide
N-(2-aminophenyl)-3,4-dimethoxybenzenesulfonamide.
N-(2-aminophenyl)-4-toluenesulfonamide
N-(2-aminophenyl)-4-fluorobenzenesulfonamide
N-(2-aminophenyl)-4-nitrobenzenesulfonamide The representative compounds as shown by the general formula(12) which are raw materials for syntheses include:

5-methylisoxazole-4-carboxylic acid
5-ethylisoxazole-4-carboxylic acid
3-ethyl-5-methylisoxazole-4-carboxylic acid
5-ethyl-3-methylisoxazole-4-carboxylic acid
3,5-diethylisoxazole-4-carboxylic acid
3,5-dimethylisoxazole-4-carboxylic acid
1,3-dimethyl-1H-pyrazole-4-carboxylic acid
2-methylthiazole-4-carboxylic acid
2,5-dimethyloxazole-4-carboxylic acid
N-methyl-1H-imidazole-4-carboxylic acid
N-(t-butoxycarbonyl)-L-proline
N-(t-butoxycarbonyl)-D-proline
N-(t-butoxycarbonyl)thiazolidine-4-carboxylic acid
N-methylpiperidine-3-carboxylic acid
N-(t-butoxycarbonyl)piperidine-4-carboxylic acid
N-(t-butoxycarbonyl)piperidine-3-carboxylic acid
N-(t-butoxycarbonyl )piperidine-2-carboxylic acid
cyclopropane carboxylic acid
cyclobutane carboxylic acid
cyclopentane carboxylic acid
cyclohexane carboxylic acid
1-metyl-2-pyrrole carboxylic acid The sulfonamide derivatives represented by the general formula(1) or the pharmaceutically acceptable salts thereof may be administered orally or parenterally(systemic or local effect)for medical use either alone or in various preparation forms such as pulver, granule, tablet, and injection manufactured by mixing with pharmaceutically acceptable additives such as vehicle, excipient, diluent, and solubilizer. Preparations should contain 0.1–100% by weight of the compounds of the present invention or the pharmaceutically acceptable salts thereof depending on the preparation forms. The doses should be determined depending on administration routes, patients' ages, and disease symptoms to protect or cure from. The dose, for example, by oral administration for an adult is 0.1 mg–2,000 mg/day, and is preferably 1 mg–1,000 mg/day in one or more times per day.

The sulfonamide derivatives represented by the general formula(1) and the pharmaceutically acceptable salts thereof have tubulin polymerization inhibitory activity, and are useful as anticancer agents and preventives or remedies for rheumatism. Rheumatism herein includes, for example, inflammatory rheumatism such as rheumatoid artiritis and osteoarthritis etc.

EXAMPLE

The present invention will now be described more in details by way of examples, provided that the present invention should not be limited by these examples. The efficiency of the compounds according to the present invention will be demonstrated by way of test examples with respect to pharmacological test results of the representative compounds. NMR values were measured by 200 Mz NMR with tetramethylsilane set as an internal standard.

Example 1

N-[2-(4-Methoxybenzenesulfonamide)phenyl]-5-methyl-4-isoxazole Carboxamide

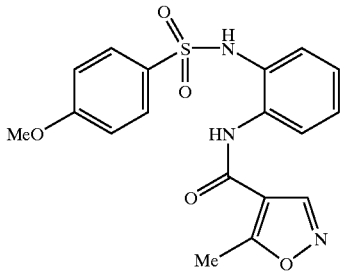

To the suspension of 5-methylisoxazole-4-carboxylic acid (2.70 g, 21.3 mmol) in methylene chloride (10 ml) was added pyridine(3.36 g, 42.5 mmol) under ice-cooled nitrogen atmosphere before thionyl chloride(2.53 g, 21.3 mmol) was added to dropwise, and then the solution was stirred at the same temperature for 30 min. To the resultant solution was added the solution of N-(2-aminophenyl)-4-methoxybenzene sulfonamide(JPLaid-Open No.39256/1993)(4.93 g, 17.7 mmol) in methylene chloride(20 ml), and the solution was left to return back to ambient temperature gradually before it was stirred overnight. The reaction solution was added to aqueous saturated sodium bicarbonate, and then subject to extraction by chloroform. The organic layer was dried over anhydrous sodium sulfate, and then concentrated to obtain the crude crystal. It was purified by recrystallization from ethanol to yield 4.50 g of the titled compound.

NMR (CDCl$_3$) ppm: 2.80 (3H, s), 3.85 (3H, s), 6.53–6.59 (2H, m)6.89 (2H, d, J=9.0 Hz), 6.94 (1H, m), 7.28 (1H, dt, J=1.5, 7.6 Hz), 7.59 (2H, d, J=9.0 Hz), 8.08 (1H, dd, J=1.4, 8.2 Hz), 8.20 (1H, s)8.96 (1 H, br s). MS (FAB, POS) m/z: 388 [M+H]$^+$.

Example 2

N-[2-(4-Methoxybenzenesulfonamide)phenyl]-3-dimethyl-4-(1H-pyrazole)carboxamide

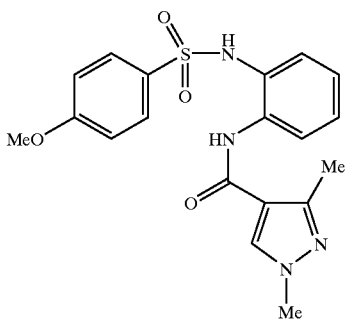

Like the Example 1 process, 1,3-dimethyl-1H-pyrazole-4-carboxylic acid (1.54 g, 11.0 mmol) was made to react with N-(2-aminophenyl)-4-methoxy benzene sulfon amide (2.70 g, 10.0 mmol) to yield 1.54 g of the titled compound.

NMR (CDCl$_3$) ppm: 2.54 (3H, s), 3.84 (3H, s), 3.87 (3H, s), 6.57 (1H, dd, J=1.4, 7.9 Hz), 6.81–6.92 (3H, d+m, J=9.0 Hz), 6.97 (1H, br s), 7.20 (1H, m), 7.59 (2H, d, J=9.0 Hz), 7.85 (1H, s)8.20 (1H, dd, J=1.4, 8.3 Hz), 8.65 (1H, br s). MS (FAB, POS) m/z: 401 [M+H]$^+$.

Example 3

N-[2-(4-Methoxybenzenesulfonamide)phenyl]-2-methyl-4-thiazole Carboxamide

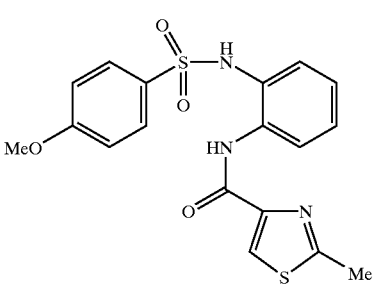

To the suspension of 5-methylthiazole-4-carboxylic acid (510 mg, 3.6 mmol) in methylene chloride(3.6 ml) was added pyridine(295 mg, 3.6 mmol)at ambient temperature before thionyl chloride(473 mg, 4.0 mmol) was added to dropwise. After 30 min, the resultant solution was added to the solution of N-(2-aminophenyl)-4-methoxybenzenesulfonamide(1.00 g, 3.6 mmol) in methylene chloride (7.2 ml) with pyridine(378 mg, 3.6 mmol) further added thereto, before it was stirred overnight. To the reaction solution was added water and ethyl acetate to extract. The organic layer was washed with aqueous saturated sodium bicarbonate, dried over anhydrous magnesium sulfate, and then concentrated to obtain the crude crystal. It was washed with diethyl ether and purified by recrystallization from isopropyl alcohol to yield 390 mg of the titled compound.

NMR (DMSO-d$_6$) ppm: 2.79 (3H, s)3.77 (3H, s), 6.84 (1 H, dd, J=1.5, 7.9 Hz), 6.95 (2H, d, J=9.0 Hz), 7.03 (1H, dt, J=1.5, 7.9 Hz), 7.28 (1H, dt, J=1.5, 8.2 Hz), 7.58 (2H, d, J=9.0 Hz),8.13 (1H, dd, J=1.5, 8.2 Hz), 8.25 (1H, s), 9.68 (1H, br s)10.00 (1H, br s). MS (FAB, PGS) m/z: 404 [M+H]$^+$.

Example 4

N-[2-(4-Methoxybenzenesulfonamide)phenyl]-3-methyl-4-isothiazole Carboxamide

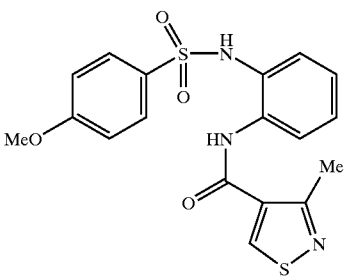

Like the Example 3 process, 3-methylisothiazole-4-carboxylic acid (510 mg, 3.7 mmol) was made to react with N-(2-aminophenyl)-4-methoxybenzene sulfon amide(1.00 g, 3.6 mmol) to yield 390 mg of the titled compound.

NMR (DMSO-d$_6$) ppm: 2.56 (3H, s), 3.75 (3H, s), 6.91 (2H, d, J=9.0 Hz), 7.11–7.23 (3H, m), 7.53 (2H, d, J=9.0 Hz), 7.66 (1H, d, J=7.6 Hz)9.41 (1H, br s)9.42 (1H, s)9.47 (1H, br s). MS (FAB, POS) m/z : 404 [M+H]$^+$.

Example 5

N-[2-(4-Methoxybenzenesulfonamide)phenyl]-2,5-dimethyl-4-oxazole Carboxamide

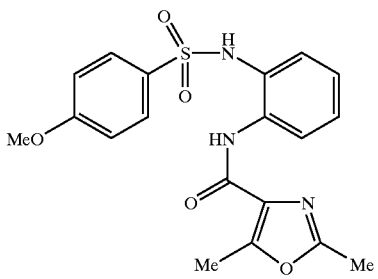

Like the Example 1 process, 2,5-dimethyloxazole-4-carboxylic acid (1.40 g, 9.9 mmol) was made to react with N-(2-aminophenyl)-4-methoxybenzene sulfonamide(2.50 g, 9.0 mmol) to yield 1.90 g of the titled compound.

NMR (CDCl$_3$) ppm: 2.45 (3H, s), 2.64 (3H, s), 3.80 (3H, s), 6.76 (2H, d, J=9.0 Hz), 7.11–7.42 (4H, m), 7.56 (2H, d, J=9.0 Hz), 7.76 (1H, br s), 8.62 (1H, br s). MS (FAB, POS) m/z :402 [M+H]$^+$.

Example 6

N-[2-(4-Methoxybenzenesulfonamide)phenyl]-1-methyl-1H-imidazole-4-carboxamide

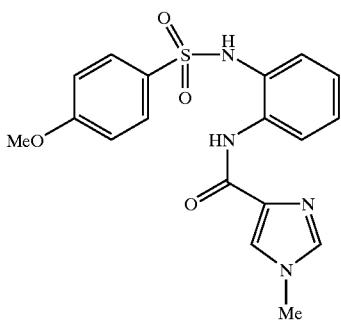

To the suspension of N-methyl-1H-imidazole-4-carboxylic acid(594 mg, 3.3 mmol) in methylene chloride(3 ml) was added pyridine(569 mg, 7.2 mmol) under ice-cooled nitrogen atmosphere be before thionyl chloride(428 mg, 3.6 mmol) was added to dropwise, and then the solution was stirred at the same temperature for 30 min. To the resultant solution was added the solution of N-(2-aminophenyl)-4-methoxy benzenesulfonamide(834 mg, 3.0 mmol) in methylene chloride(3 ml), and the solution was left to return back to ambient temperature gradually before it was stirred overnight. The reaction solution was added to aqueous saturated sodium bicarbonate, and then subject to extraction by chloroform. The organic layer was dried over anhydrous sodium sulfate, and then concentrated to obtain the residue. It was purified by silicagel chromatography (chloroform:methanol=19:1) to yield 100 mg of the titled compound.

NMR (DMSO-d$_6$) ppm: 3.74 (3H, d, J=4.2 Hz), 3.80 (3H, s), 6.67 (1H, dd, J=1.3, 7.9 Hz), 6.88–7.09 (3H, d+m, J=8.9 Hz), 7.18–7.37 (2H, m)7.61 (2H, d, J=8.9 Hz), 7.75–7.85 (3H, m), 8.22 (1H, dd, J=1.3, 8.2 Hz), 9.63 (1H, br s)9.88 (1H, br s). MS (FAB, POS) m/z: 387 [M+H]$^+$.

Example 7

N-[2-(p-Toluenesulfonamide)phenyl]-5-methyl-4-isoxazole Carboxamide

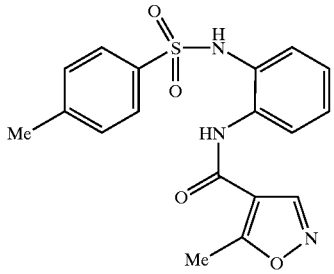

Like the Example 1 process, 5-methylisoxazole-4-carboxylic acid (667 mg, 5.3 mmol) was made to react with N-(2-aminophenyl)-4-toluene sulfonamide(1.31 g, 5.0 mmol) to yield 1.19 g of the titled compound.

NMR (DMSO-d$_6$) ppm: 2.29 (3H, s), 2.67 (3H, s)7.13–7.25 (5H, d+m, J=8.3 Hz), 7.45–7.55 (3H, d+m, J=8.3 Hz) 8.82 (1H, s)9.30 (1H, s)9.44 (1H, s). MS (FAB, POS) m/z: 372 [M+H]$^+$.

Example 8

N-[2-(Benzenesulfonamide)phenyl]-5-methyl-4-isoxazole Carboxamide

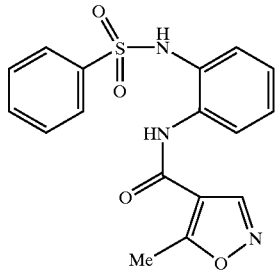

Like the Example 1 process, 5-methylisoxazole-4-carboxylic acid (667 mg, 5.3 mmol) was made to react with N-(2-aminophenyl)-benzene sulfonamide(1.23 g, 5.0 mmol) to yield 690 mg of the titled compound.

NMR (DMSO-d$_6$) ppm: 2.66 (3H, s), 7.14–7.2 6 (3H, m), 7.37–7.65 (6H, m), 8.84 (1H, s), 9.32 (1H, s)9.56 (1H, s) MS (FAB, POS) m/z: 358 [M+H]$^+$.

Example 9

N-[2-(4-Fluorobenzenesulfonamide)phenyl]-5-methyl-4-isoxazole Carboxamide

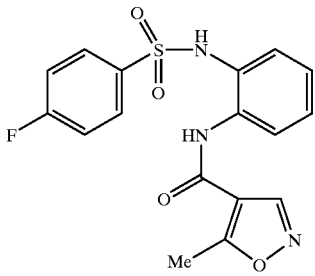

Like the Example 1 process, 5-methylisoxazole-4-carboxylic acid (667 mg, 5.3 mmol) was made to react with N-(2-aminophenyl)-4-fluorobenzene sulfonamide (1.33 g, 5.0 mmol) to yield 300 mg of the titled compound.

NMR (DMSO-$d_6$) ppm: 2.6 6 (3H, s)7.16–7.28 (5H, m), 7.49 (1H, m), 7.59–7.69 (2H, m), 8.85 (1H, s), 9.31 (1H, br s), 9.56 (1H, br s). MS (FAB, POS) m/z: 376 [M+H]$^+$.

Example 10

N-[2-(4-Nitrobenzenesulfonamide)phenyl]-5-methyl-4-xazole Carboxamide

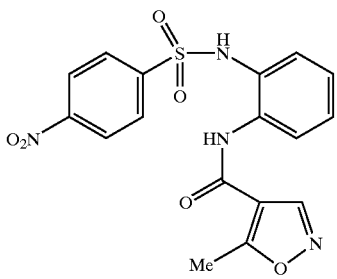

Like the Example 1 process, 5-methylisoxazole-4-carboxylic acid (667 mg, 5.3 nmuol) was made to react with N-(2-aminophenyl)-4-nitrobenzene sulfonamide (1.46 g, 5.0 mmol) to yield 330 mg of the titled compound.

NMR (DMSO-$d_6$) ppm: 2.59 (3H, s)7.20–7.33 (3H, m), 7.43 (1H, m), 7.81 (2H, d, J=8.8 Hz), 8.21 (2H, d, J=8.8 Hz)8.82 (1H, s), 9.27 (1H, br s), 9.80 (1H, br s). MS (FAB, POS) m/z: 403 [M+H]$^+$.

Example 11

N-[2-(3,4-Dimethoxybenzenesulfonamide)phenyl]-5-methyl-4-isoxazole Carboxamide

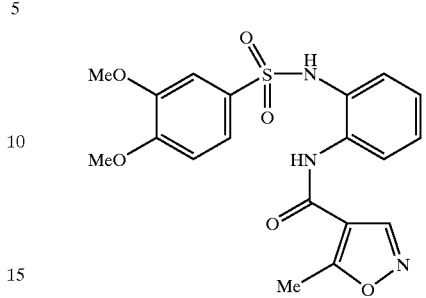

Like the Example 6 process, 5-methylisoxazole-4-carboxylic acid (667 mg, 5.3 mtmol) was made to react with N-(2-aminophenyl)-3,4-dimethoxybenzene sulfonamide (1.54 g, 5.0 mmol) to yield 750 mg of the titled compound. NMR (DMSO-$d_6$) ppm: 2.6 3 (3H, s)3.5 6 (3H, s),3.75 (3 H, s),6.89 (1H, d, J=8.6 Hz),6.97 (1H, d, J=2.2 Hz 7.10–7.31 (5H, m), 7.50 (1H, m), 8.80 (1H, s), 9.23 (1H, s)9.32 (1H, s). MS (FAB, POS) m/z :418 [M+H]$^+$.

Example 12

N-[2-(4-Methoxybenzenesulfonamide)phenyl]-(L)-prolinamide HCl Salt

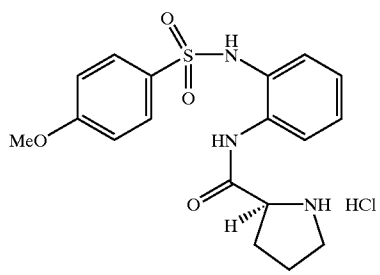

To the suspension of N-(t-butoxycarbonyl)-L-prolin (474 mg, 2.2 mmol) in methylene chloride(5 ml) was added pyridine(348 mg, 4.4 mmol) under ice-cooled nitrogen atmosphere before thionyl chloride(367 mg, 2.2 mmol) was added to dropwise, and then the solution was stirred at the same temperature for 30 min. To the resultant solution was added the solution of N-(2-aminophenyl)-4-methoxy benzenesulfonamide(556 mg, 2.0 mmol), and the solution was left to return back to ambient temperature gradually before it was stirred overnight. The reaction solution was concentrated to obtain the residue, to which 4N-HCl/dioxane(5.0 ml,20.0 mmol) was added before it was stirred at ambient temperature for 2 hrs. The reaction solution was concentrated to obtain the residue, which was purified by silicagel chromatography (chloroform:methanol=19:1)and HP-20 (0 to 90% aqueous methanol solution) to yield 210 mg of the titled compound.

NMR (CD$_3$OD) ppm: 2.05–2.22 (2H, m), 2.31 (1H, m), 2.55 (1H, m), 3.34–3.55 (2H, m), 3.86 (3H, s), 4.55 (1H, t, J=8.0 Hz), 6.70 (1H, d, J=7.9 Hz), 7.00 (2H, d, J=8.9 Hz), 7.02 (1H, m), 7.25 (1H, m), 7.58 (2H, d, J=8.9 Hz), 7.78 (1H, m). MS (FAB, POS) m/z: 376 [M+H]$^+$.

Example 13

N-[2-(4-Methoxybenzenesulfonamide)phenyl]-3,5-dimethyl-4-isoxazole Carboxamide

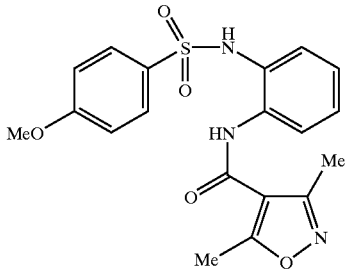

Like the Example 6 process, 3,5-dimethylisoxazole-4-carboxylic acid (846 mg, 6.0 mmol) was made to react with N-(2-aminophenyl)-4-methoxybenzene sulfonamide (1.39 g, 5.0 mmol) to yield 60 0 mg of the titled compound.

NMR (DMSO-$d_6$) ppm: 2.41 (3H, s), 2.63 (3H, s), 3.8 2 (3H, s), 6.83 (1H, dd, J=1.4, 8.0 Hz), 6.99–7.09 (3H, m), 7.22 (1H, dt, J=1.5, 8.0 Hz), 7.60 (2H, d, J=9.0 Hz), 7.86 (s), 9.10 (1H, brs), 9.49 (1H, brs). MS (FAB, POS) m/z: 402 [M+H]$^+$.

Example 14

N-[2-(4-Methoxybenzenesulfonamide)phenyl]-5-ethyl-4-isoxazole Carboxamide

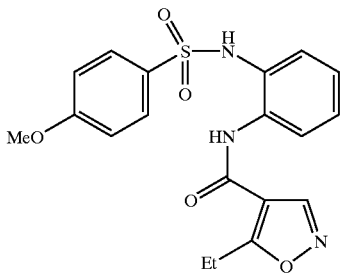

Like the Example 1 process, 5-ethylisoxazole-4-carboxylic acid (846 mg, 6.0 mmol) was made to react with N-(2-aminophenyl)-4-methoxybenzene sulfonamide (1.39 g, 5.0 mmol) to yield 1.04 g of the titled compound.

NMR (CDCl$_3$) ppm: 1.39 (3H, t, J=7.6 Hz), 3.23 (2H, q, J=7.6 Hz), 3.85 (3H, s), 6.58 (1H, dd, J=1.4, 8.0 Hz), 6.63 (1H, s), 6.89 (2H, d, J=9.0 Hz), 6.94 (1H. d t, J=1.5, 7.7 Hz), 7.28 (1H, m), 7.58 (2H, d, J=9.0 Hz), 8.07 (1H, dd, J=1.4, 8.0 Hz), 8.60 (1H, br s). MS (FAB, POS) m/z: 402 [M+H]$^+$.

Example 15

(±)-N-[2-(4-Methoxybenzenesulfonamide)phenyl]-4-thiazolidine Carboxamide HCl Salt

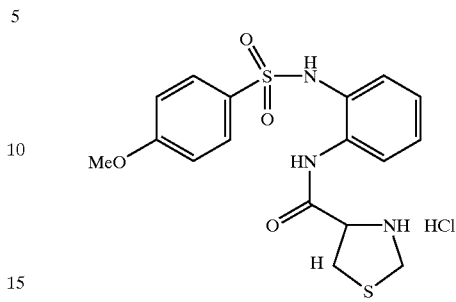

To the suspension of N-(t-butoxycarbonyl)thiazolidine-4-carboxylic acid(1.0 g, 6.0 mmol) in methylene chloride(10 ml) was added pyridine(1.02 g, 12.0 mmol) under ice-cooled nitrogen atmosphere before thionyl chloride(718 mg, 6.0 mmol) was added to dropwise, and then the solution was stirred at the same temperature for 30 min. To the resultant solution was added the solution of N-(2-aminophenyl)-4-methoxy benzenesulfonamide(1.39 g, 5.0 mmol), and the solution was left to return back to ambient temperature gradually before it was stirred overnight. The reaction solution was concentrated to obtain the residue, to which ethyl acetate and aqueous saturated sodium bicarbonate were added to extract. The organic layer was dried over anhydrous sodium sulfate and concentrated to obtain the residue, which was purified by silicagel chromatography (chloroform:methanol=19:1). To the resultant residue was added 4 N-HCl/dioxane(12.5 ml, 50.0 mmol) before it was stirred at ambient temperature for 2 hrs. The reaction solution was concentrated to obtain the crude crystal, which was purified by recrystallization from methanol to yield 1.05 g of the titled compound.

NMR (CD$_3$OD) ppm: 3.11 (1H, dd, J=7.5, 10.7 Hz), 3.40 (1H, dd, J=4.0, 10.7 Hz), 3.86 (3H, s), 4.16 (1H, d, J=9.7 Hz), 4.32 (1H, d, J=9.7 Hz), 4.33 (1H, dd, J=2.0, 7.5 Hz), 6.64 (1H, dd, J=1.5, 7.0 Hz), 6.90–7.04 (3H, m+d, J=9.0 Hz), 7.24 (1H, dt, J=1.5, 8.0 Hz), 7.59 (2H, d, J=9.0 Hz), 8.02 (1H, dd, J=1.4, 8.0 Hz). MS (FAB, POS) m/z: 394 [M+H]$^+$.

Example 16

(±)-N-[2-(4-Methoxybenzenesulfonamide)phenyl]-3-(N-methyl piperidine)carboxamide HCl Salt

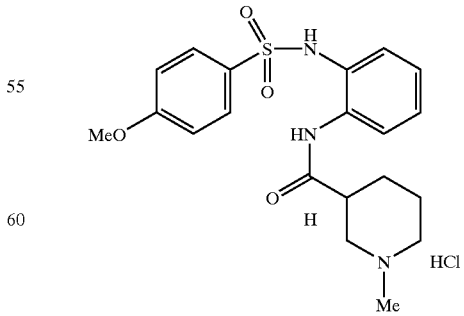

To the suspension of N-methylpiperidine-3-carboxylic acid(537 mg, 3.0 mmol) in methylene chloride(10 ml) was added pyridine(767 mg, 9.0 mmol) under ice-cooled nitrogen atmosphere before thionyl chloride(359 mg, 3.0 mmol) was added to dropwise, and then the solution was stirred at the same temperature for 30 min.

To the resultant solution was added the solution of N-(2-aminophenyl)-4-methoxy benzenesulfonamide(695 mg, 2.5 mmol), and the solution was left to return back to ambient temperature gradually before it was stirred overnight. The reaction solution was concentrated to obtain the residue, which was purified by HP-20 (gradient with 0 to 90% aqueous mathanol solution) to yield 550 mg of the titled compound.

NMR (DMSO-d6) ppm: 1.42 (1H, m), 1.80–2.02 (3H, m), 2.79 (3H, d, J=3.4 Hz), 2.85–3.50 (5H, m), 3.82 (3H, s) 7.01–7.20 (5H, d+m, J=9.0 Hz), 7.51–7.59 (3H, m+d, J=9.0 Hz), 9.45 (1H, br s), 9.65 (1H, br s). MS (FAB, POS) m/z: 440 $[M+H]^+$.

Example 17

N-[2-(4-Methoxybenzenesulfonamide)phenyll-(D)-prolinamide HCl Salt

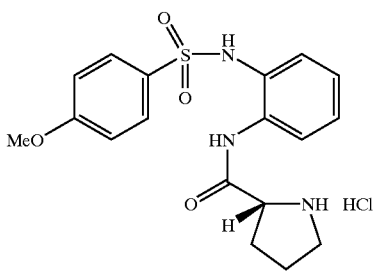

Like the Example 12 process, N-(t-butoxycarbonyl)-D-prolin (1.29 g, 6.0 mmol) was made to react with N-(2-aminophenyl)-4-methoxybenzene sulfonamide (1.39 g, 5.0 mmol) to yield 150 mg of the titled compound.

NMR (CD$_3$OD) ppm: 1.90–2.08 (2H, m), 2.16 (1H, m), 2.42 (1H, m), 3.20–3.36 (2H, m), 3.87 (3H, s), 4.23 (1H, d d, J=6.0, 8.9 Hz), 6.68 (1H, dd, J=1.5, 8.0 Hz), 6.94–7.03 (3H, d+m, J=9.0 Hz), 7.25 (1H, d t, J=1.5, 8.0 Hz), 7.59 (2H, d, J=9.0 Hz), 7.90 (1H, dd, J=1.4, 8.2 Hz). MS (FAB, POS) m/z:376 $[M+H]^+$.

Example 18

N-[2-(4-Methoxybenzenesulfonamide)phenyl)]-4-piperidine carboxamide HCl Salt

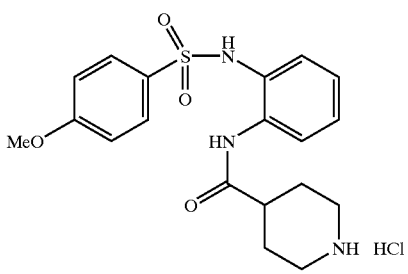

To the suspens ion of N-(t-butoxycarbonyl)piperidine-4-carboxylic acid(1.38 g, 6.0 mmol) in methylene chloride(20 ml) was added pyridine(1.02 g, 12.0 mmrol) under ice-cooled nitrogen atmosphere before thionyl chloride(718 mg, 6.0 mmol) was added to dropwise, and then the solution was stirred at the same temperature for 30 min. To the resultant so lution was added the solution of N-(2 nophenyl-4-methoxy benzenesulfonamide(1.39 g, 5.0 mmol), and the solution was left to return back to ambient temperature gradually before it was stirred overnight. The reaction solution was concentrated to obtain the residue, to which ethyl acetate and aqueous saturated sodium bicarbonate were added to extract. The organic layer was stdried over anhydrous sodium sulfate and concentrated to obtain the residue, to which 4 N-HCl/dioxane (15.0 ml, 60.0 mmol) was added before it was stirred at ambient temperature for 2 hrs. The reaction solution was concentrated to obtain the crude crystal, which was washed with isopropyl alcohol to yield 1.52 g of the titled compound.

NMR (DMSO-d$_6$) ppm: 1.67–2.00 (4H, m), 2.6 1 (1H, m), 2.83–3.06 (2H, m), 3.25–3.44 (3H, m), 3.80 (3H, s), 6.97–7.20 (5H, d+m, J=8.9 Hz), 7.55 (2H, d, J=8.9 Hz), 7.64 (1H, d, J7.7 Hz)r8.65 (1H, br s), 8.90 (1H, br s). MS (FAB, POS) m/z: 390 $[M+H]^+$.

Example 19

(±)-N-[2-(4-methoxybenzenesulfonamide)phenyl]-3-piperidine Carboxamide HCl salt

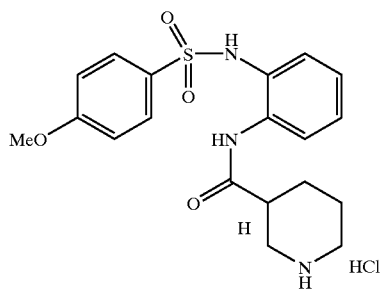

Like the Example 18 process, N-(t-butoxycarbonyl) piperidine-3-carboxylic acid(1.38 g, 6.0 mmol) was made to react with N-(2-aminophenyl)-4-methoxybenzene sulfonamide (1.39 g, 5.0 mmol) to yield 900 mg of the titled compound, where the corresponding residue was purified by silicagel chromatography (chloroform:methanol=19:1)and HP-20 (gradient with 0 to 90% aqueous methanol solution).

NMR (CD$_3$OD) ppm: 1.82–2.21 (5H, m), 2.91–3.48 (4H, m), 3.86 (3H, s), 6.84 (1H. dd, J=1.5, 7.9 Hz), 6.98 (2H, d, J=8.9 Hz), 7.04 (1H, dt, J=1.5, 7.9 Hz), 7.23 (1H, dt, J=1.4, 8.0 Hz), 7.56 (2H, d, J=8.9 Hz), 7.69 (1H, dd, J=1.4, 8.0 Hz). MS (FAB, POS) m/z: 390 $[M+H]^+$.

Example 20

(±)-N-[2-4-Methoxybenzenesulfonamide)phenyl]-2piperidine Carboxamide HCl Salt

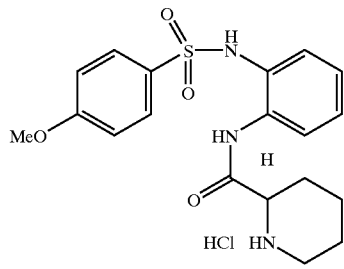

Like the Example 18 process, N-(t-butoxycarbonyl) piperidine-3-carboxylic acid(1.38 g, 6.0 mmol) was made to react with N-(2-aminophenyl)-4-methoxybenzenesulfonamide(1.39 g, 5.0 mmol) to yield 1.24 g of the titled compound, where the corresponding residue was purified by HP-20 (gradient with 0 to 90% aqueous methanol solution).

NMR (CD$_3$OD) ppm: 1.65–2.07 (5H, m), 2.42 (1H, m), 3.09 (1H, m), 3.45 (1H, m), 3.85 (3H, s), 4.10 (1H, m), 6.70 (1H, dd, J=1.5, 7.9 Hz), 6.99 (2H, d, J=9.0 Hz), 7.02 (1H, m), 7.25 (1H, dt, J=1.5, 8.0 Hz), 7.59 (2H, d, J=9.0 Hz), 7.83 (1H, dt, J=1.4, 8.0 Hz). (FAB, POS) m/z: 390 [M+H]$^+$.

Example 21

N-[2-(4-Methoxybenzenesulfonamide)phenyl]-5-methyl-4-oxazole Carboxamide

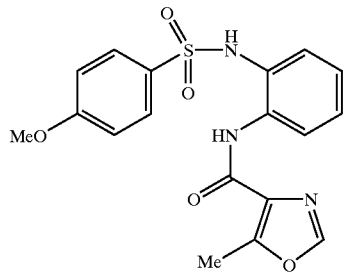

Like the Example 1 process, 5-methyloxazole-4-carboxylic acid (315 mg, 2.5 mmol) was made to react with N-(2-aminophenyl)-4-methoxybenzene sulfonamide(584 mg, 2.1 mmol) to yield 430 mg of the titled compound.

NMR (DMSO-d$_6$) ppm: 2.64 (3H, s), 3.80 (3H, s), 6.76 (1H, dd, J=1.4, 7.9 Hz), 6.94 (2H, d, J=9.0 Hz), 6.98 (1H, dt, J=1.5, 7.9 Hz), 7.24 (1H, dt, J=1.5, 8.2 Hz), 7.56 (2H, d, J=9.0 Hz), 8.11 (1H, dd, J=1.4, 8.2 Hz), 8.42 (1H, s), 9.63 (1H, br s), 9.75 (1H, br s). MS (FAB, POS) m/z: 388 [M+H]$^+$.

Example 22

N-[2-(4-Methoxybenzenesulfonamide)phenyl]-cyclohexyl Carboxamide

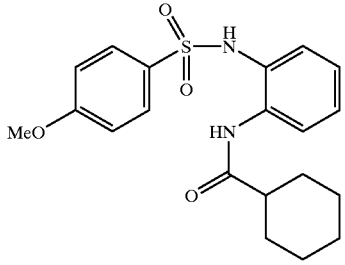

To the solution of N-(2-aminophenyl)-4-methoxybenzene sulfon amide(1.39 g, 5.0 mmol) in tetrahydrofuran(20 ml) was dropwise added cyclohexane carbonyl chloride(748 mg, 5.1mmol) under ice-cooled nitrogen atmosphere, and then the solution was left to return back to ambient temperature gradually before it was stirred overnight. The reaction solution was concentrated to obtain the residue, which was dissolved in ethyl acetate and washed with aqueous sodium bicarbonate. The organic layer was dried over anhydrous sodium sulfate, and concentrated to obtain the crude crystal, which was purified by recrystallization from ethanol to yield 1.10 g of the titled compound.

NMR (DMSO-d$_6$) ppm: 1.1 6–1.43 (5H, m)N 1.60–1.83 (5H, m), 2.16 (1H, m), 3.81 (3H, s), 6.95 7.20 (5H, m+d, J=8.8 Hz), 7.46–7.67 (3H, m+d, J=8.8 Hz), 9.02 (1H, s), 9.2 3 (1H, s). MS (FAB, POS) m/z: 389 [M+H]$^+$.

Example 23

N-[2-(4-Methoxybenzenesulfonamide)phenyl]-cyclopropyl Carboxamid

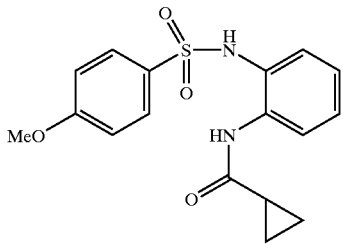

Like the Example 22 process, N-(2-aminophenyl)-4-methoxybenzene sulfonamide(1.39 g, 5.0 mmol) was made to react with cyclopropane carbonyl chloride(533 mg, 5.1 mmol) to yield 820 mg of the titled compound.

NMR (DMSO-d$_6$) ppm 0.75–0.86 (4H, m), 1.60 (1H, m), 3.80 (3H, s), 6.99 (2H, d, J=9.0), 7.05–7.20 (3H, m), 7.45–7.54 (3H, m), 9.20 (1H, br s), 9.45 (1H, br s). MS (FAB, POS) m/z:347 [M+H]$^+$.

Example 24

N-(2-(4-Methoxybenzenesulfonamide)phenyl]-cyclobutyl Carboxamid

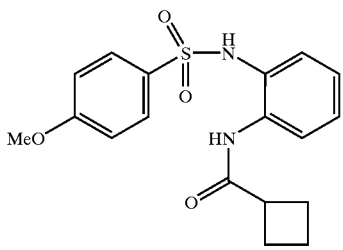

Like the Example 22 process, N-(2-aminophenyl)-4-methoxybenzene sulfonamide(1.39 g, 5.0 mmol) was made to react with cyclobutane carbonyl chloride(597 mg, 5.1 mmol) to yield 1.54 g of the titled compound.

NMR (DMSO-d$_6$) ppm: 1.75–2.25 (6H, m), 3.10 (1H, m), 3.79 (3H, s), 6.97–7.22 (5H, m), 7.43–7.60 (3H, m), 9.00 (1H, br s), 9.28 (1H, br s). MS (FAB, POS) m/z: 361 [M+H]$^+$.

Example 25

N-2-(4-Methoxybenzenesulfonamide)phenyl]-cyclopentyl Carboxamid

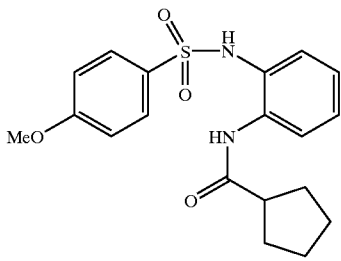

Like the Example 22 process, N-(2-aminophenyl)-4-methoxybenzene sulfonamide(1.39 g, 5.0 mmol) was made to react with cyclopentane carbonyl chloride(666 mg, 5.1 mmol) to yield 1.02 g of the titled compound.

NMR (DMSO-d6) ppm: 1.50–1.90 (8H, m), 2.65 (1H, m), 3.80 (3H, s), 6.97–7.22 (5H, m), 7.46–7.62 (3H, m), 9.15 (1H, br s), 9.26 (1H, br s) MS (FAB, POS) m/z: 375 [M+H]$^+$.

Example 26

N-[2-(4-Methoxybenzenesulfonamide)phenyl]-N-methyl-2-pyrrole Carboxamide

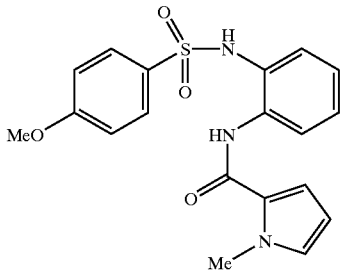

Like the Example 1 process, 1-methyl-2-pyrrole carboxylic acid (625 mg, 5.0 mmol) was made to react with N-(2-aminophenyl)-4-methoxybenzene sulfon amide(1.39 g, 5.0 mmol) to yield 1.55 g of the titled compound.

NMR (DMSO-d6) ppm: 3.77 (3H, s), 3.84 (3H, s), 6.14 (1H, dd, J=2.6, 4.0 H z), 6.84 (1H, dd, J=2.0, 4.0 Hz), 6.93 (2H, d, J=9.0 Hz), 6.97–7.09 (3H, m), 7.22 (1H, dt, J=2.0, 8.1 Hz), 7.57 (2H, d, J=9.0 Hz), 7.76 (1H, dd, J=1.3, 8.0 Hz), 9.22 (1H, br s), 9.54 (1H, br s). MS (FAB, POS) m/z: 386 [M+H]$^+$.

Example 27

N-[2-(4-Methoxybenzenesulfonamide)phenyl]-3-ethyl-5-methyl-4-isoxazole Carboxamide

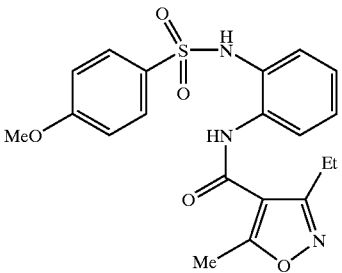

To the suspension of 3-ethyl-5-methylisoxazole-4-carboxylic acid(930 mg, 6.0 mmol) in methylene chloride (10 ml) was added pyridine (0.97 ml, 12.0 mmol) under ice-cooling by stirring before thionyl chloride(0.44 ml, 6.0 mmol) was added to dropwise. After 30 min, to the resultant solution was added N-(2-aminophenyl)-4-methoxy benzenesulfonamide(1.39 g, 5.0 mmol) under ice-cooling, and the solution was left to return back to ambient temperature gradually before it was stirred overnight. To the reaction solution was added water and ethyl acetate to extract. The organLic layer was washed with aqueous saturated sodium bicarbonate, 2N-HCl, and water, and then dried over anhydrous magnesium sulfate. The resultant solution was concentrated to obtain the crude residue, which was purified by silicagel chromatography(hexane:ethyl acetate=2:1) to yield 1.95 g of the titled compound.

NMR (DMSO-d6) ppm: 1.24 (3H, t, J=7.5 Hz), 2.63 (3H, s), 2.84 (2H, q, J=7.5 Hz), 3.83 (3H, s), 6.84 (1H, dd, J=1.5, 7.9 Hz), 6.95–7.08 (3H, m), 7.21 (1H, d t, J=1.5, 7.9 Hz), 7.60 (2H, d, J=8.8 Hz), 7.86 (1H, dd, J=1.3, 8.1 Hz), 9.10 (1H, br s), 9.45 (1H, br s). MS (FAB, POS) m/z: 416 [M+H]$^+$.

Example 28

N-[2-(4-Methoxybenzenesulfonamide)phenyl]-5-ethyl-3-methyl-4-isoxazole Carboxamide

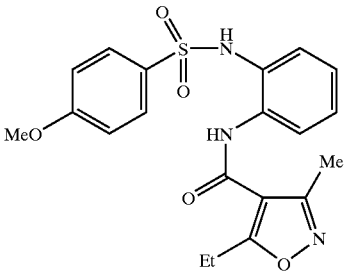

Like the Example 27 process, 5-ethyl-3-methylisoxazole-4-carboxylic acid (930 mg, 6.0 mmol) was made to react with N-(2-aminophenyl)-4-methoxybenzene sulfon amide (1.39 g, 5.0 mmol) to yield 1.96 g of the titled compound.

NMR (DMSO-d$_6$) ppm: 1.28 (3H, t, J=7.6 Hz), 2.43 (3H, s), 3.04 (2H, q, J=7.6 Hz), 3.83 (3H, s), 6.80 (1H, dd, J=1.5, 7.9 Hz), 6.95–7.08 (3H, m), 7.21 (1H, d t, J=1.5, 7.9 Hz), 7.60 (2H, d, J=8.8 Hz), 7.89 (1H, dd, J=1.3, 8.1 Hz), 99.10 (1H, br s), 9.50 (1H, br s). MS (FAB, POS) m/z: 416 [M+H]$^+$.

Example 29

N-[2-(4-Methoxybenzenesulfonamide)phenyl]-3,5-diethyl-4-isoxazole Carboxamide

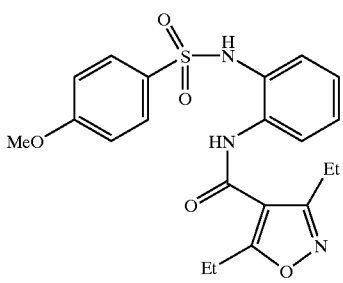

Like the Example 27 process, 3,5-diethyl-isoxazole-4-carboxylic acid (1.01 g, 6.0 mmol) was made to react with N-(2-aminophenyl)-4-methoxybenzene sulfon amide(1.39 g, 5.0 mmol) to yield 1.82 g of the titled compound.

NMR (DMSO-d6) ppm: 1.25 (3H, t, J=7.7 Hz), 1.29 (3H, t, J=7.7 Hz), 2.85 (2H, q, J=7.7 Hz), 3.03 (2H, q, J=7.7 Hz), 3.83 (3H, s), 6.82 (1H, dd, J=1.5, 7.9 Hz) 6.96–7.10 (3H, m), 7.22 (1H, dt, J=1.5, 7.9 Hz), 7.60 (2H, d, J=8.8 Hz), 7.88 (1H, dd, J=1.3, 8.1 Hz), 9.18 (1H, br s), 9.48 (1H, br s). MS (FAB, POS) m/z: 430 [M+H]$^+$.

Example 30

N-[2-(4-Methoxybenzenesulfonamide)phenyl]-5-isopropyl-3-methyl-4-isoxazole Carboxamide

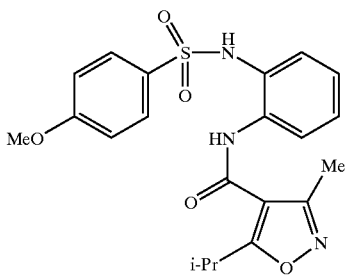

Like the Example 27 process, 5-isopropyl-3-methylisoxazole-4-carboxylic acid (1.01 g, 6.0 mmol) was made to react with N-(2-aminophenyl)-4-methoxybenzene sulfon amide(1.39 g, 5.0 mmol) to yield 1.59 g of the titled compound.

NMR (DMSO-d6) ppm: 1.31, 1.34 (2×3H, each s), 2.43 (3H, s), 3.61 (1H, m), 3.85 (3H, s), 6.78 (1H, dd, J=1.5, 7.9 Hz), 6.96–7.08 (3H, m), 7.22 (1H, dt, J=1.5, 7.9 Hz), 7.61 (2H, d, J=9.0 Hz), 7.9 2 (1H, dd, J=1.3, 8.1 Hz), 9.12 (1H, br s), 9.50 (1H, br s). MS (FAB, POS) m/z: 430 [M+H]$^+$.

Example 31

N-[2-(4-Methoxybenzenesulfonamide)phenyl]-5-methyl-3-phenyl-4-isoxazole Carboxamide

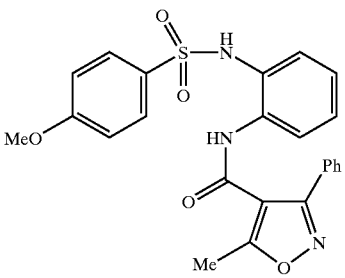

Like the Example 27 process, 5-methyl-3-phenylisoxazole-4-carboxylic acid (500 mg, 2.46 mmol) was made to react with N-(2-aminophenyl)-4-methoxybenzene sulfonamide(570 mg, 2.05 mmol) to yield 400 mg of the titled compound.

NMR (DMSO-d6) ppm: 2.41 (3H, s), 3.80 (3H, s), 6.90–7.24 (5H, m), 7.53–7.61 (5H, m), 7.73–7.88 (3H, m), 9.33 (1H br s), 9.70 (1H, br s). MS (FAB, POS) m/z: 464 [M+H]$^+$.

Example 32

N-[2-(4-Methoxybenzenesulfonamide)phenyl]-3-methyl-5-phenyl-4-isoxazole Carboxamide

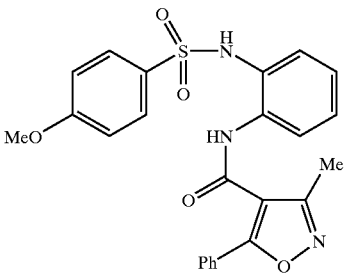

Like the Example 27 process, 3-methyl-5-phenylisoxazole-4-carboxylic acid (1.22 g, 6.0 mmol) was made to react with N-(2-aminophenyl)-4-methoxybenzene sulfonamide(1.39 g, 5.0 mmol) to yield 1.12 g of the titled compound.

NMR (DMSO-d6) ppm: 2.65 (3H, s), 3.80 (3H, s), 6.87–7.22 (5H m), 7.46–7.61 (5H, m), 7.68–7.78 (3H, m), 9.34 (1H, br s), 9.54 (1H, br s). MS (FAB, POS) m/z: 464 [M+H]$^+$.

The pharmacological effects of the compounds of the present invention will be demonstrated concretely by way of test examples. Abbreviations used in the test examples are as follows, CTP: Cytidine 5'-triphosphate
EGTA: Ethylene glycol bis(2-aminoethylether)
GTP: Guanosine 5'-triphosphate
MES: 2-morpholinoethane sulfonic acid
RB: Reaction buffer Test Example 1

Tubulin polymerization inhibitory test using microtubule proteins originated from swine brain: Microtubule proteins was extracted from swine brain by the Shelansky method (Tanpakusitu jikkenhou, Zoku-Seikagaku Jikken Kouza, Vol.6, "Structure and Function of Cytoskeleton" ($1^{st}$ Vol.), Tokyo Kagaku Dojin). Polymerization of microtubule proteins was assayed by turbidity measurement.

Warming in RB(MES:100 mM, $MgCl_2$:0.5 mM, EGTA:1mM, pH6.8) containing GTP accelerates microtubule proteins, which are previously depolymerized in ice bath, to reconstruct microtubules, with increased turbidity resulted in. Change in turbidity can be measured by an absorptiometer. The compounds of the present invention were dissolved in dimetylsulfoxide to prepare their test solutions. To 245 $\mu$l of a RB solution containing microtubule proteins(2 mg/ml)and GTP(1 mM) was added 5$\mu$l of either an above test solution or dimethylsulfoxide to prepare a sample, which was incubated at 37° C. for 30 min. Absorbance at 340 nm was measured by an absorptiometer, and Inhibitory Rate was calculated by the equation as described below to determine $IC_{50}$, the concentration of a test compound required to achieve 50% of inhibitory rate. Absorbance at 340 nm of the compound was previously measured.

$$\text{Inhibitory Rate}(\%) = [1 - (T - C_{min})/(C_{max} - C_{min})] \times 100$$

where T is absorbance of the incubated sample with a test compound, $C_{max}$ is absorbance of the incubated sample without the compound, and $C_{min}$ is the non-incubated sample without the compound. The $IC_{50}$ values are shown in the Table 1.

TABLE 1

| Test compound (EXAMPLE No.) | $IC_{50}$ ($\mu$g/ml) |
| --- | --- |
| 1 | 1.2 |
| 2 | 36 |
| 3 | 38 |
| 4 | 1.4 |
| 6 | 39 |
| 7 | 5.1 |
| 8 | 230 |
| 9 | 150 |
| 11 | 150 |
| 13 | 1.4 |
| 14 | 1.65 |
| 15 | 1.85 |
| 21 | 4.7 |
| 22 | 1.9 |
| 23 | 1.20 |
| 24 | 1.15 |
| 25 | 1.55 |
| 26 | 1.90 |
| 27 | 1.85 |
| 28 | 1.30 |
| 29 | 3.95 |
| 30 | 3.30 |

(note):
$IC_{50}$ of colchicine (made by Wako Junyaku, Tokyo) is 4.0 $\mu$g/ml.

Test Example 2

Anti-tumor in Vitro Test Using the A2780 (Humane Ovarian Cancer Cell)

A2780 cells that were suspended on a RPMI 1640 culture medium containing 10% calf serum, penicillin (50 U/ml), and streptomycin (50 $\mu$g/ml were seeded in a 96 well flat microplate by 1000 cells (0.2 ml) well, and cultured in a 5% carbon dioxide atmospheric incubator at 37° C. for 1 day. The compounds of the present invention that were dissolved in dimetylsulfoxide anddiluted with a RPMI 1640 containing 10% calf serum to prepare the samples, provided that dimetylsulfoxide was restricted to 0.2% and below in concentration.

The Supernatant liquids of the above A2780 cells wells were removed by aspiration, and then each 0.2 ml of the prepared samples were added to the wells, which were incubated in a 5% carbon dioxide atmospheric incubator at 37° C. for 3 days. After the incubation, each 0.01 ml of MTT solutions(3-(4,5-dimethylthiazole-2-yl)-2,5-dipheny-ltetra zolium bromide, 5 mg/ml) were added to the wells, which were incubated for another 2 hrs. After the supernatant liquids in the wells were removed by aspiration, the formazans formed in the wells were dissolved in 0.1 ml of dimetylsulfoxide, and absorbances at 540 nm were measured by a micro plate reader to determine indices of live cells counts in the wells. Inhibitory Rate was calculated by the equation as described below to determine $IC_{50}$, the concentration of a test compound required to achieve 50% of inhibitory rate.

$$\text{Inhibitory Rate}(\%) = [(C - T)/C] \times 100$$

where T is absorbance in the well with a test compound and C is absorbance in the well without the compound. The $IC_{50}$ values are shown in the Table 2.

TABLE 2

| Test compound (EXAMPLE No.) | $IC_{50}$ ($\mu$g/ml) |
| --- | --- |
| 1 | 0.023 |
| 2 | 0.58 |
| 3 | 0.22 |
| 4 | 0.017 |
| 5 | 7.2 |
| 6 | 0.14 |
| 7 | 0.20 |
| 8 | 6.7 |
| 9 | 13 |
| 11 | 0.68 |
| 12 | 9.7 |
| 13 | 0.010 |
| 14 | 0.036 |
| 15 | 0.025 |
| 17 | 1.4 |
| 20 | 6.8 |
| 21 | 0.079 |
| 22 | 0.14 |
| 23 | 0.006 |
| 24 | 0.006 |
| 25 | 0.05 |
| 26 | 0.034 |
| 27 | 0.034 |
| 28 | 0.013 |
| 29 | 0.14 |
| 30 | 0.16 |
| 31 | 0.30 |
| 32 | 0.62 |

Test Example 3

Prophylactic Experiment of Collagen-induced Arthritis in Mice

The suspension of M. tuberculosis H37RA in Freund incomplete adjuvant (2 mg/ml) was mixed with 0.3% typeII collagen (extracted from bovine articular cartilage, Collagen Gijutsu KensyU Kai) in their equal amounts to form an emulsion, 0.1 ml of which was injected subcutaneously into the base of the tail of mice to sensitize it. After twenty-one days, 0.3% type II collagen was diluted with physiological saline solution to the one sixth concentration of the solution, 0.2 ml of which was injected intraperitoneally to sensitize secondarily. The mice that the first sensitizations caused to fall into arthritis were excluded from the test. The suspensions of the compounds(in the Example 13, 27, and 28) in 0.5% sodium carboxy methylcellulose (CMC—Na) were administrated orally to the test group mice once a day for 5 weeks from the day after the second sensitization. 0.5% CMC—Na solutions were administrated to the control group mice to be compared with. Each group was composed of eight mice. Daily symptoms in the mice limbs were observed to determine stratified scores (0 to 4, hence maximum 16). Scores and their standards are as follows.

0: No symptom

1: Tumefaction or rubor in only one finger(or heel)

2: Tumefaction or rubor in two or above fingers (or heels) or in parts of fore (or hind) paw(s)

3: Tumefaction or rubor in the wholes of fore (or hind) paw(s) including joints

4: Ankylosis in the joints of finger(s) (or heel(s)) or fore (or hind) paw(s)

The results on the last day of this test are shown in the Table 3.

TABLE 3

| Test compound (EXAMPLE No.) | Dose mg/kg | Averaged score |
| --- | --- | --- |
| Control | 0 | 8.5 ± 1.7 |
| 13 | 25 | 2.3 ± 0.8* |
| 13 | 50 | 0.4 ± 0.4** |
| 27 | 50 | 1.7 ± 1.1* |
| 28 | 50 | 3.0 ± 1.1* |

\*\*: $p < 0.005$, \*: $p < 0.05$

Compared with the control group, the test groups of the compunds of the present invention show significant prophylactic effect on collagen-induceded arthritis model in mice which is an animal model for rheumatoid arthritis.

Furthermore, blood tests(blood cell count, GOT)and histological observations of main organs executed on the last day suggested that the compounds gave little toxicity on bone marrow, liver, heart, lung, spleen, pancreas, and gastrointestine.

INDUSTRIAL APPLICABILITY

The compounds of the present invention are confirmed to have tubulin polymerization inhibitory activity and antitumor effect. The prophylactic experiment of collagen-induced arthritis in mice which is an animal model for rheumatoid arthritis confirms them to have excellent anti-rheumatic effect. Furthermore, they have low toxicity and 5 weeks' continuous administrations as executed in the Test Example give no death. Blood tests and histological observations suggest that the compounds give little toxicity on bone marrow; liver, heart, lung, spleen, pancreas, and gastrointestine. Therefor, the compounds of the present invention are useful as low toxic anti-tumor agents and preventives or remedies for rheumatism.

What is claimed is:

1. A compound of formula (1)

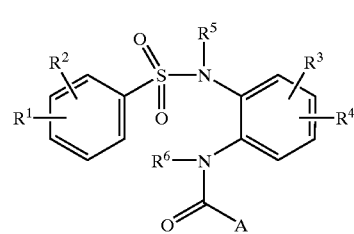

(1)

(wherein $R^1$ and $R^2$ may be the same or different and each independently represents a hydrogen atom, a halogen atom, a lower alkoxy group, a nitro group, a hydroxy group; each $R^3$, $R^4$, $R^5$ and $R^6$ represents a hydrogen atom;

A represents a 5-membered heterocyclic hydrocarbon group (except triazoyl group) having at least two unsaturated bonds and containing at least two heteroatoms, and being optionally substituted by a lower alkyl group or phenyl group, whose ring members include at least 1 nitrogen atom and may include and atom(s) selected from the group consisting of nitrogen atom, oxygen atom, and sulfur atom, or pharmaceutically acceptable salts thereof.

2. A compound as defmed in claim 1, wherein $R^1$ is a lower alkoxy group, and $R^2$ represents a hydrogen atom.

3. A compound according to claim 2, wherein A represents A 5-membered heterocyclic group (except triazolyl group) whose ring members include at least 1 nitrogen atom and may include any atom(s)selected from the group consisting of nitrogen atom, oxygen atom, and sulfur atom.

4. A compound according to claim 3, wherein A represents an isoxazolyl group.

5. A compound according to claim 4, wherein A represents a 4-isoxazolyl group which has at least one lower alkyl group at the 3- and 5- position.

6. A compound according to claim 5, wherein $R^1$ is a lower alkoxy group which is located at the para-position.

* * * * *